United States Patent
Guan et al.

(10) Patent No.: US 11,020,060 B2
(45) Date of Patent: Jun. 1, 2021

(54) MONITORING SYSTEM AND MONITORING METHOD

(71) Applicant: BOE TECHNOLOGY GROUP CO., LTD., Beijing (CN)

(72) Inventors: Enhui Guan, Beijing (CN); Lu Tong, Beijing (CN); Shuo Chen, Beijing (CN); Tianyue Zhao, Beijing (CN); Xianzhen Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/440,541

(22) Filed: Jun. 13, 2019

(65) Prior Publication Data
US 2020/0029915 A1 Jan. 30, 2020

(30) Foreign Application Priority Data
Jul. 27, 2018 (CN) .......................... 201810845761.5

(51) Int. Cl.
A61B 5/00 (2006.01)
A61B 7/00 (2006.01)
G08B 21/18 (2006.01)
G08B 21/24 (2006.01)
G10L 25/63 (2013.01)
A61B 5/11 (2006.01)

(52) U.S. Cl.
CPC ............ *A61B 5/7282* (2013.01); *A61B 5/742* (2013.01); *A61B 5/7405* (2013.01); *A61B 5/746* (2013.01); *A61B 7/003* (2013.01); *G08B 21/182* (2013.01); *G08B 21/24* (2013.01); *G10L 25/63* (2013.01); *A61B 5/1118* (2013.01); *A61B 2503/04* (2013.01)

(58) Field of Classification Search
CPC combination set(s) only.
See application file for complete search history.

(56) References Cited

U.S. PATENT DOCUMENTS

2014/0318699 A1* 10/2014 Longinotti-Buitoni ...................... A61B 5/6805 156/247
2016/0174728 A1* 6/2016 Karp .................... A47D 15/008 5/655

* cited by examiner

*Primary Examiner* — Thomas S McCormack
(74) *Attorney, Agent, or Firm* — Nath, Goldberg & Meyer; Joshua B. Goldberg

(57) ABSTRACT

Disclosed are a monitoring system and a monitoring method. The monitoring system includes: a collection device, configured to collect feature data of a baby; and a processor, coupled to the collection device and configured to receive the feature data collected by the collection device, determine a state condition of the baby according to the feature data, and output prompt information corresponding to the state condition.

11 Claims, 5 Drawing Sheets

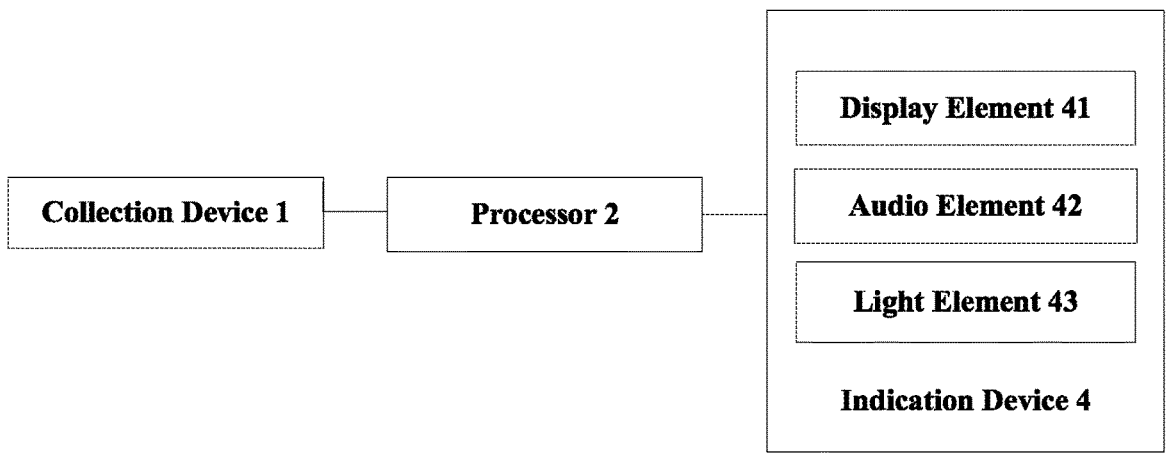
FIG. 4
FIG. 5
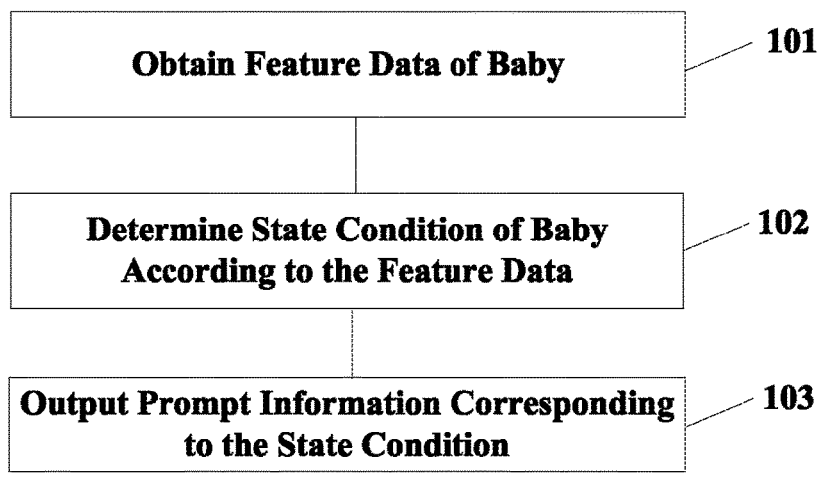
FIG. 6

MONITORING SYSTEM AND MONITORING METHOD

CROSS-REFERENCE TO RELATED APPLICATIONS

The present application claims priority to Chinese Patent Application No. 201810845761.5, entitled "Monitoring System and Monitoring Method", filed to the Chinese Intellectual Property Office on Jul. 27, 2018, the disclosure of which is incorporated herein by reference.

FIELD OF THE INVENTION

The present disclosure relates to, but is not limited to, the field of electronic technologies, and in particular, to a monitoring system and a monitoring method.

BACKGROUND

In the case where a baby feels uncomfortable, he or she may be crying since he or she is not able to express his or her needs through language. However, parents cannot quickly determine the specific reasons of the baby's discomfort. At this point, the parents usually judge by screening, which may waste a lot of time for investigation. Especially in the evening, it may not only affect people's rest, but also cause pain to the baby.

SUMMARY

In view of the above, the embodiments of the present disclosure provide a monitoring system and a monitoring method which are mainly used to determine a specific reason of baby's crying.

To achieve above objective, according to a first aspect, there is provided a monitoring system in an embodiment of the disclosure, including: a collection device, configured to collect feature data of a baby; and a processor, coupled to the collection device and configured to receive the feature data collected by the collection device, determine a state condition of the baby according to the feature data, and output prompt information corresponding to the state condition.

In an optional embodiment, the monitoring system further includes a storage device, coupled to the processor and configured to store a preset database, the preset database storing preset feature data corresponding to the state condition of the baby, and the processor is configured to determine a state condition corresponding to the preset feature data as the state condition of the baby in the case where the feature data falls within a range of the preset feature data.

In an optional embodiment, the monitoring system further includes a timing device, coupled to the processor and configured to obtain crying time information of the baby according to the feature data of the baby, and the processor is configured to receive the crying time information and correct the state condition corresponding to the preset feature data in the preset database or output a correction reminder information in the case where the crying time information exceeds a preset crying time threshold.

In an optional embodiment, the monitoring system further includes an input device coupled to the storage device and configured to input correction information to correct the state condition corresponding to the preset feature data in the preset database.

In an optional embodiment, the collection device includes at least one of a sound collection element, a displacement collection element and a pressure collection element, wherein the sound collection element is configured to collect sound data of the baby as the feature data; the displacement collection element is configured to collect displacement data of the baby as the feature data; and the pressure collection element is configured to collect pressure data of the baby as the feature data.

In an optional embodiment, the monitoring system further includes an indication device coupled to the processor and configured to receive the prompt information output by the processor and output an indication corresponding to the prompt information.

In an optional embodiment, the indication device includes at least one of a display element, an audio element and a light element, wherein the display element is coupled to the processor and configured to receive the prompt information output from the processor and provide a display reminder according to the prompt information; the audio element is coupled to the processor and configured to receive the prompt information output from the processor and provide a sound reminder according to the prompt information; the light element is coupled to the processor and configured to receive the prompt information output from the processor and provide a light reminder according to the prompt information.

According to a second aspect, there is provided a monitoring method in an embodiment of the disclosure, including: obtaining feature data of a baby; determining a state condition of the baby according to the feature data; and outputting prompt information corresponding to the state condition.

In an optional embodiment, the method further includes: creating a preset database in which preset feature data corresponding to the state condition of the baby is stored, and the step of determining a state condition of the baby according to the feature data includes: detecting the presence of preset feature data corresponding to the feature data; and determining a state condition corresponding to the preset feature data as the state condition of the baby in the case where the feature data falls within a range of the preset feature data.

In an optional embodiment, the method further includes: obtaining a crying time of the baby; detecting, according to the state condition, whether the crying time exceeds a preset crying time threshold; and correcting the state condition corresponding to the preset feature data in the preset database, or outputting correction reminder information.

In an optional embodiment, the method further includes: obtaining correction information; and correcting the state condition corresponding to the preset feature data in the preset database according to the correction information.

In an optional embodiment, the feature data of the baby includes at least one of displacement data of the baby, pressure data of the baby, and sound data of the baby.

In an optional embodiment, the prompt information includes at least one of image prompt information, sound prompt information, and light prompt information.

An embodiment of the present disclosure provides a monitoring system for automatically determining the specific reason of baby crying. In the prior art, parents may not quickly determine the specific reason of the baby's discomfort. At this point, parents usually judge by screening, which will waste a lot of time for investigation. Especially in the evening, it will not only affect people's rest, but also cause pain to the baby. Compared with the prior art, the monitoring system according to the embodiment of the present disclosure includes: a collection device and a processor, wherein the collection device is configured to collect feature data of the baby, and the processor is capable of receiving the feature data collected by the collection device, determining the state condition of the baby based on the feature data, and outputting the prompt information corresponding to the state condition. In this way, the parents can know the reason why the baby is crying according to the prompt information and take corresponding measures according to the reason of crying, thereby saving treatment time.

BRIEF DESCRIPTION OF THE DRAWINGS

FIG. 4 is a block diagram of a monitoring system according to another embodiment of the present disclosure;
FIG. 5 is a block diagram of a monitoring system according to another embodiment of the present disclosure;
FIG. 6 is a flow chart of a monitoring method according to an embodiment of the present disclosure.

DETAILED DESCRIPTION OF THE EMBODIMENTS

In order to further explain the technical means and functions of the present disclosure for achieving the desirable purpose of the disclosure, the monitoring system according to the present disclosure and the specific embodiments, structures, features and functions thereof will be described in detail below with reference to the accompanying drawings and preferred embodiments.

Figure 1:
FIG. 1 is a block diagram of a monitoring system according to an embodiment of the present disclosure.

As shown in FIG. 1, an embodiment of the present disclosure provides a monitoring system, including:
a collection device 1 configured to collect feature data of a baby; and
a processor 2 coupled to the collection device 1 and configured to receive the feature data collected by the collection device 1, determine a state condition of the baby according to the feature data, and output prompt information corresponding to the state condition.

Here, the above-mentioned collection device 1 may collect the feature data of the baby to determine the state condition of the baby, wherein the feature data may include, but is not limited to, data information such as sound data, pressure data, displacement data, and the like, and accordingly the collection device 1 may include sensors corresponding to the above feature data, such as a sound collector, a pressure detector, a displacement detector, and the like. The feature data can reflect the baby's active movements, such as crying, waving, kicking, turning over, etc. Then, according to the magnitude and intensity of these activities, the specific state condition of the baby such as hot feeling, cold feeling, excretion, and hunger can be judged. The above-mentioned collection device 1 can be disposed around the baby, for example, a blanket on which the baby sleeps or a baby bed, so that the information of the baby can be accurately obtained and the interference of environmental factors on the feature data can be reduced.

Here, the above processor 2 is mainly configured to judge the state condition of the baby based on the feature data as described above. For example, if the baby continues kicking, the baby may be subjected to bedwetting. At this time, the processor 2 can judge the state condition of the baby based on the feature data and output the prompt information corresponding to the state condition. The prompt information may include display information of the display screen, sound information, light information, and the like. According to the prompt information, the parents can understand the state condition of the baby, so as to take corresponding measures. Each state condition can have a corresponding measure. For example, if the state condition is a baby bedwetting, then the corresponding measure may be changing a diaper. Therefore, the processor 2 can output treatment measure information corresponding to the state condition in addition to the prompt information corresponding to the state condition, so that new parents can more easily cope with the baby crying.

An embodiment of the present disclosure provides a monitoring system for automatically determining the specific reason of baby crying. In the related art, parents may not quickly determine the specific reason of the baby's discomfort. At this point, parents usually judge by screening, which will waste a lot of time for investigation. Especially in the evening, it will not only affect people's rest, but also cause pain to the baby. Compared with the prior art, the monitoring system according to the embodiment of the present disclosure includes: a collection device and a processor, wherein the collection device is configured to collect feature data of the baby, and the processor is capable of receiving the feature data collected by the collection device, determining the state condition of the baby based on the feature data, and outputting the prompt information corresponding to the state condition. In this way, the parents can know the reason why the baby is crying according to the prompt information and take corresponding measures according to the reason of crying, thereby saving treatment time.

Figure 2:
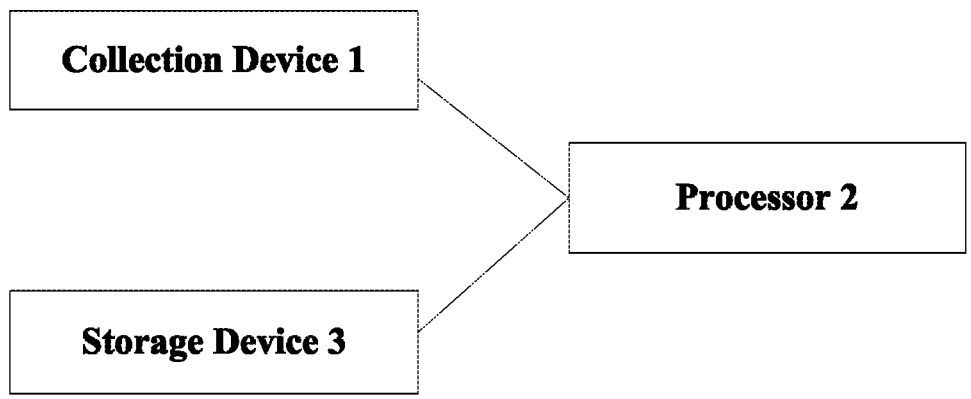
FIG. 2 is a block diagram of a monitoring system according to another embodiment of the present disclosure.

The processor 2 can judge the state condition of the baby based on the feature data. Optionally, in some embodiments, as shown in FIG. 2, the above monitoring system further includes: a storage device 3 coupled to the processor 2 and configured to store a preset database, the preset database storing a plurality of kinds of preset feature data corresponding to different state conditions of the baby. At this time, the processor 2 is configured to determine a state condition corresponding to the preset feature data as the state condition of the baby in the case where the feature data falls within a range of the preset feature data. In this embodiment, the storage device 3 may be a data storage device such as a hard disk and a non-volatile memory; the storage device 3 is mainly configured to store the preset database, such that the processor 2 can obtain corresponding data information in real time through the preset database. Here, the preset database stores preset feature data and a state condition corresponding to the preset feature data. When the processor 2 receives the feature data collected by the collection device 1, the processor 2 can judge whether the feature data falls within the range of the preset feature data. If the feature data falls within the range of the preset feature data, the processor 2 may determine the state condition corresponding to the preset feature data as the state condition of the baby to output to the parents of the baby so that the parents of the baby can quickly cope with baby's crying. In such a manner, the reason for the baby's crying can be determined quickly and accurately, so as to timely cope with the baby's crying problem.

Figure 10:
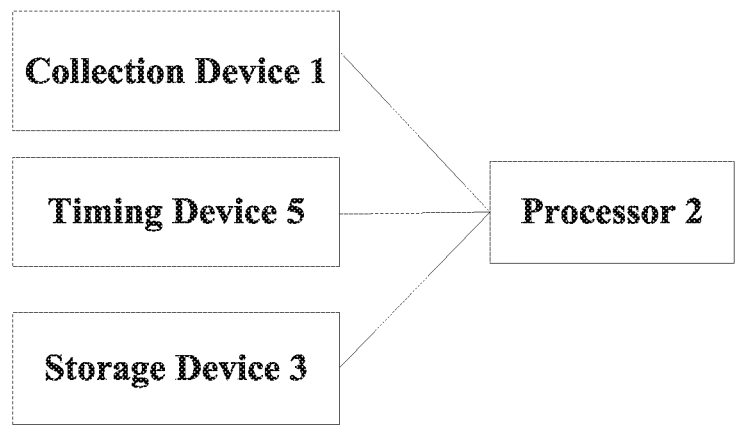
FIG. 10 is a block diagram of a monitoring system according to another embodiment of the present disclosure.

In order to ensure the accuracy of the above-mentioned monitoring system for judgment of the state condition of the baby, in some embodiments, as shown in FIG. 10, the monitoring system may further include a timing device 5 coupled to the processor and configured to obtain crying time information of the baby according to the feature data of the baby; the processor is configured to receive the crying time information and correct the state condition corresponding to the feature data in the preset database or output a correction reminder information in the case where the crying time information exceeds a preset crying time threshold.

In this embodiment, it is possible to judge whether the baby is crying based on the feature data. For example, when the baby's sound data (for example, decibel) exceeds a set value, it can be determined that the baby is crying, and when the baby's sound data is lower than the set value, it can be determined that the baby stops crying. In addition, a plurality of determination manners may be used, which are not specifically limited herein. Here, the time of crying can be a period of time from the baby starting crying to the baby stopping crying. The feature data is used to accurately calculate the baby's crying time.

In general, when parents cope with baby's crying in the right way, the time taken thereon may be relatively short. Therefore, the duration of coping with the baby's crying can be used to judge whether the state condition information of the baby provided by the system is correct, so as to timely correct the information in the preset database to ensure the accuracy of the information in the preset database. For example, when it is known that the baby is moved to the mother by the feature data (for example, the displacement data), the state condition corresponding to the preset feature data in the preset database is a hunger state condition, and the hunger state condition can be fed back to the baby's parents while the crying time of baby is calculated. The baby's parents will cope with the baby's crying in response to the hunger state condition. When the baby stops crying, the baby's parents can judge whether their treatment is correct according to the crying time of the baby. If the baby's crying time exceeds the preset crying time threshold, such as 20 minutes, it can be indicated that the treatment of the baby's parents is not correct. In this case, the state condition (hunger state condition) corresponding to the preset feature data in the preset database may be incorrect. At this point, there is a need to modify this state condition. For example, the state condition may be modified to a bedwetting state. When the state condition corresponding to the feature data occurs to baby again, the state condition fed back to the parents by the monitoring system is a state condition of bedwetting rather than the state condition of hunger. In this way, the parents can cope with the baby's crying with reference to the new state condition, so as to improve the treatment speed of the baby's parents. The monitoring system according to this embodiment can improve the accuracy of the data information in the database by continuously improving the data information in the database. In addition, different state conditions may correspond to different preset crying time thresholds. For example, the preset crying time threshold reflecting a cold or hot state condition may be 2 minutes; and the preset crying time threshold reflecting a state condition of bedwetting or hunger may be 5 minutes.

When the crying time exceeds the preset crying time threshold, in addition to automatically correcting the state of the preset feature data range by the monitoring system, the correction reminder information may also be output to remind the parents or other user to perform a manual correction. The outputting manner of correction reminder information may include, for example, a text or image reminder by using a display device or a voice reminder, which is not specifically limited herein.

Figure 11:
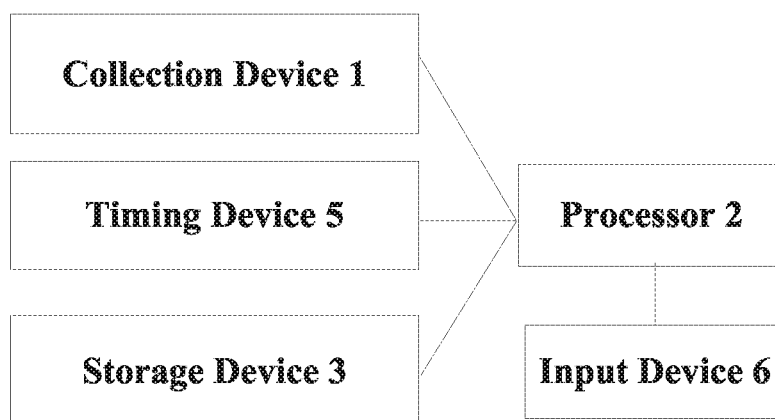
FIG. 11 is a block diagram of a monitoring system according to another embodiment of the present disclosure.

Further, as shown in FIG. 11, the monitoring system may further include an input device 6 coupled to the processor 2 and configured to input correction information from a user to correct the state condition corresponding to the preset feature data in the preset database. In this embodiment, the user can manually input the correction information through the input device 6 to correct the state condition corresponding to the preset feature data. By correction, the accuracy of judging the state condition can be further improved. The input device 6 may include, for example, a touch display device, an input keyboard, and the like, which are not specifically limited herein.

Figure 3:
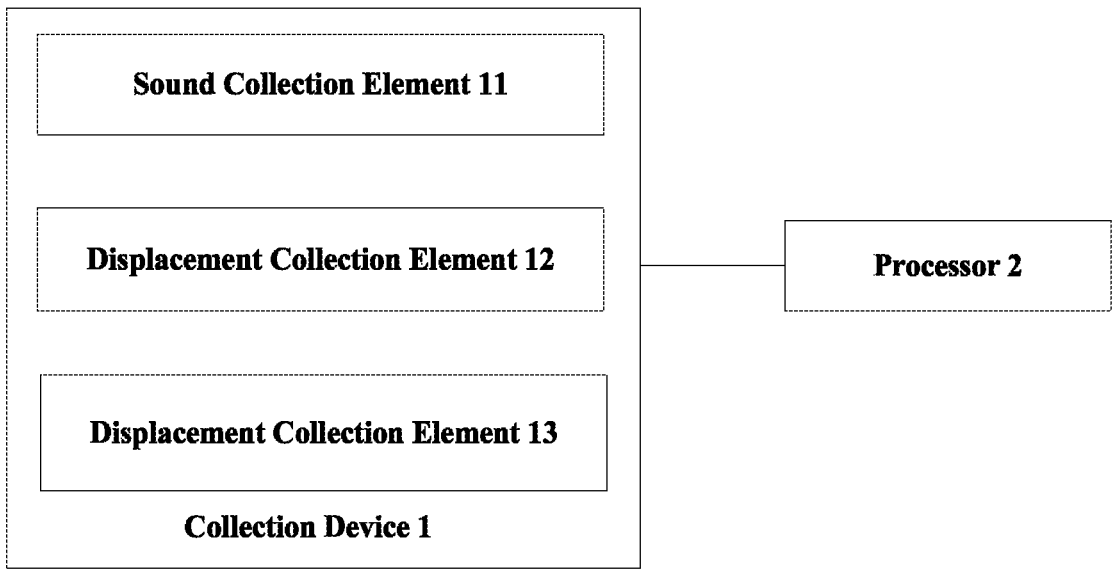
FIG. 3 is a block diagram of a monitoring system according to another embodiment of the present disclosure.

The above-described collection device 1 may include a plurality of information collection elements. In some embodiments, as shown in FIG. 3, the collection device 1 includes a sound collection element 11 configured to collect sound data of the baby as the feature data. The baby's crying usually makes a sound, such as crying or screaming sound. The different state conditions of the baby (for example, cold feeling, hot feeling, bedwetting, hunger, etc.) may make different sounds. Therefore, the processor can judge the state of the baby based on the sound data. For example, a baby may make relatively low sound when feeling hot, make relatively high sound when feeling cold, make fluctuating sound when bedwetting, and make intermittent sound when feeling hungry. Therefore, the state of the baby can be judged based on the sound data, such that the parents can quickly understand the reason of the baby's crying and improve the speed of coping with the baby crying problem. In addition, the above-described sound collection element 11 may include a sound recorder, a microphone, and the like. The sound collection element 11 can be placed in the vicinity of the baby's head to obtain clearer sound of the baby. In addition, the sound collection element 11 can also have a filtering function to filter environmental sound, such as parent's snoring sound, such that the accuracy of the sound data can be improved.

The above-described collection device 1 may include collection elements having other functions in addition to the sound collection element 11. In some embodiments, as shown in FIG. 3, the collection device 1 includes a displacement collection element 12 configured to collect displacement data of the baby as the feature data. The baby usually moves when crying. The different state conditions of the baby, such as cold feeling, hot feeling, bedwetting and hunger, may have different directions and distances of movement. Therefore, the state of the baby can be judged based on the direction and distance of the movement. For example, in the case of hunger, the baby may move to the mother; in the case of the bedwetting, the baby may move to the mother; in the case of hot feeling, the baby may move upwards; in the case of cold feeling, the baby may move downwards. Based on the direction or distance of the displacement, the state of the baby can be judged, so that the parents can quickly understand the reason of the baby's crying and improve the speed of coping with the baby crying problem. The displacement collection element 12 may include a displacement sensor, such as a digital laser displacement sensor, a photoelectric displacement sensor, and a magnetically sensitive displacement sensor, which are not specifically limited herein. For ease of detection, the displacement sensor can be placed in a mat under the baby, for example.

The above-described collection device 1 may include collection elements having other functions in addition to the sound collection element 11 and the displacement collection element 12. In some embodiments, as shown in FIG. 3, the collection device 1 may include a pressure collection element 13 configured to collect pressure data of the baby as the feature data. The baby usually wields hands and feet when crying. For example, in the case of bedwetting, the baby may raise legs and then put down; in the case of is hunger, the baby may kick aimlessly; and in the case of cold or hot feeling, the baby may move the hands and feet. The pressure data of the baby's legs can be obtained by the pressure collection element 13 to judge the movement of the baby. Through the pressure information, the state condition of the baby can be judged, so that the parents can quickly understand the reason of the baby's crying and improve the speed of coping with the baby crying problem. The pressure collection element 13 may include a pressure sensor, such as a piezoresistive pressure sensor and a piezoelectric pressure sensor, which are not specifically limited herein. The pressure sensor can be placed in a mat under the baby's legs, for example.

In some embodiments, as shown in FIG. 4, the above-described monitoring system further includes: an indication device 4 coupled to the processor 2 and configured to receive prompt information output by the processor 2 and output an indication corresponding to the prompt information. In this embodiment, the indication device 4 is configured to display indication information to the parents of the baby, such that the parents can obtain the state condition of the baby more quickly. As shown in FIG. 5, in an optional embodiment, the indication device 4 includes a display element coupled to the processor 2 and configured to receive and display the prompt information output from the processor 2. In this embodiment, the prompt information may be display information. The display information can be information displayed by displaying devices such as televisions, tablets, mobile phones, and the like. The parents of baby can obtain the state condition of the baby, such as cold feeling, hot feeling, bedwetting and hunger, through the displaying device such that the parents can obtain information more conveniently and quickly.

As shown in FIG. 5, in an optional embodiment, the indication device can include an audio element 42 coupled to the processor 2 and configured to receive the prompt information output from the processor 2 and provide a sound reminder according to the prompt information. In this embodiment, the prompt information may be audio information. For example, the audio information may be a specific prompt language, such as "baby bedwetting", or may be a specific prompt sound, such as a music sound, a reminder sound, and the like. The audio element 42 can include a speaker to play the sound to the babys parents as a reminder such that the parents can obtain the information more conveniently and quickly.

As shown in FIG. 5, in an optional embodiment, the indication device may include a light element 43 coupled to the processor 2 and configured to receive the prompt information output from the processor 2 and provide a light reminder according to the prompt information. In this embodiment, the prompt information nay be light information, such as the frequency of the light flashing and the color of the light flashing. The baby's parents can understand the state condition of the baby, such as cold feeling, hot feeling, bedwetting and hunger, according to the light information, such that the parents can obtain the information more conveniently and quickly. The light element 43 can be a signal light or an indicator light, which is not specifically limited herein.

On the other hand, as shown in FIG. 6, in an embodiment of the present disclosure, there is further provided a monitoring method, including:

Step 101: obtaining feature data of a baby;

Step 102: determining a state condition of the baby according to the feature data; and Step 103: outputting prompt information corresponding to the state condition.

The specific implementation manner of the above steps has been described in detail in the device embodiment, and the details thereof will not be described herein.

In an embodiment of the present disclosure, there is provided a monitoring method for automatically determining a specific reason of a baby crying. In the related art, the parents cannot quickly determine the specific reason of the baby's discomfort. At this point, the parents usually judge by screening, which will waste a lot of time for investigation. Especially in the evening, it may not only affect people's rest, but also cause pain to the baby. Compared with the related art, the monitoring method according to this embodiment of the present disclosure includes: obtaining feature data of the baby; determining a state condition of the baby according to the feature data; and outputting prompt information corresponding to the state condition. In this way, the parents can understand the reason why the baby is crying according to the prompt information, and perform corresponding treatment according to the reason of crying, thereby saving treatment time.

In some embodiments, for example, the feature data of the baby may include at least one of displacement data of the baby, pressure data of the baby, and sound data of the baby. In this embodiment, the specific implementations of determining the state condition of the baby by the displacement data, the pressure data and the sound data have been described in detail in the above-mentioned device embodiment, and are not specifically limited herein.

In some embodiments, the prompt information may include at least one of image prompt information, sound prompt information, and light prompt information. The prompt information has been described in detail in the above device embodiment, and is not specifically limited herein.

Figure 7:
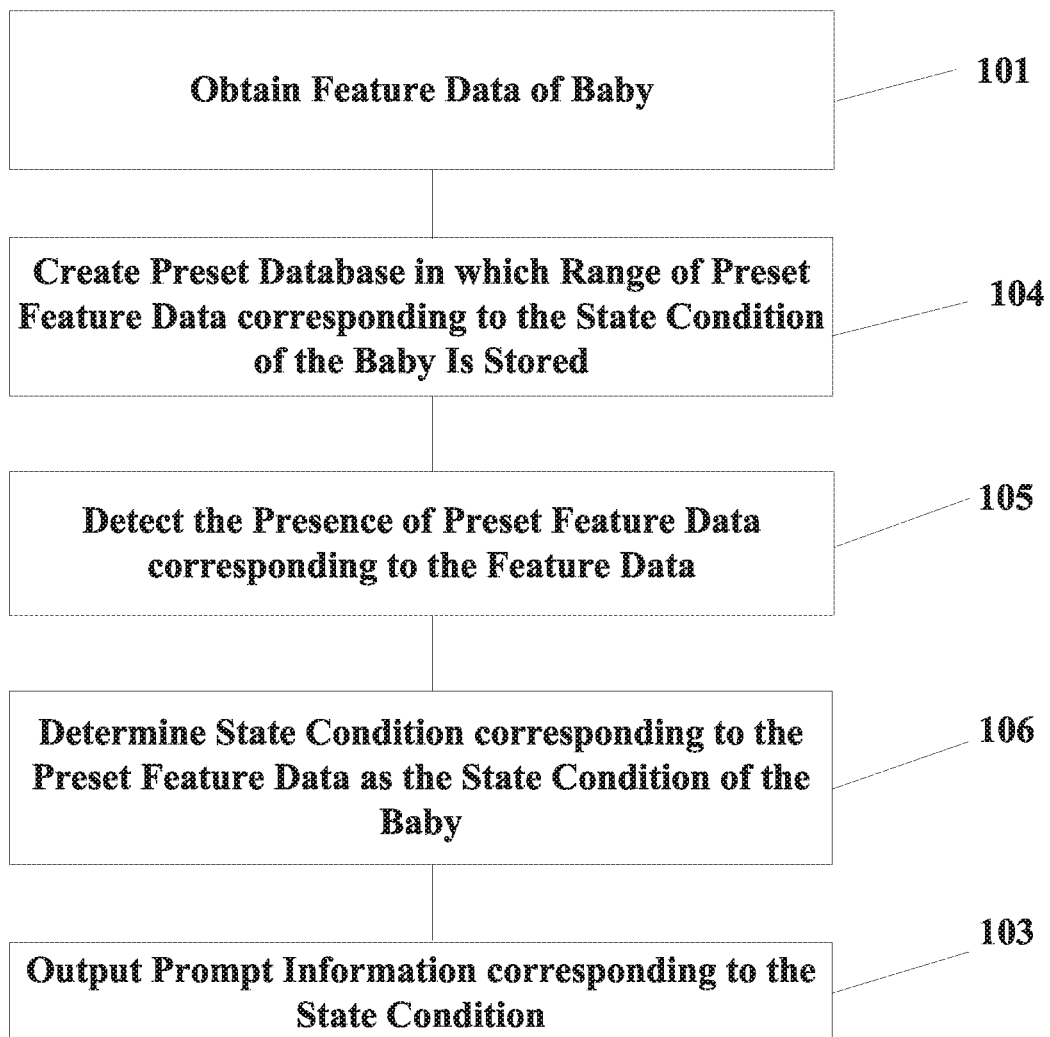
FIG. 7 is a flow chart of a monitoring method according to another embodiment of the present disclosure.

In some embodiments, as shown in FIG. 7, the above monitoring method further includes:

Step 104: creating a preset database in which preset feature data corresponding to the state condition of the baby is stored.

The step of determining a state condition of the baby according to the feature data may further include:

Step 105: detecting the presence of preset feature data corresponding to the feature data; and Step 106: determining a state condition corresponding to the preset feature data as the state condition of the baby in the case where the feature data falls within a range of the preset feature data.

In this embodiment, a range of the preset feature data may include, for example, sound of 60-80 decibels and displacement distance of 30-50 cm. The above monitoring method can be used to judge whether the feature data of the baby falls within the range of the corresponding preset feature data. For example, if the sound of the baby reaches 70 decibels and the range of the preset feature data is 60-80 decibels, the monitoring method can be used to determine that the state condition of the baby is a state condition corresponding to the preset feature data. The preset database stores a plurality of types of the preset feature data, and each type of the preset feature data corresponds to at least one baby condition, such as cold feeling, hot feeling, bedwetting and hunger.

Figure 8:
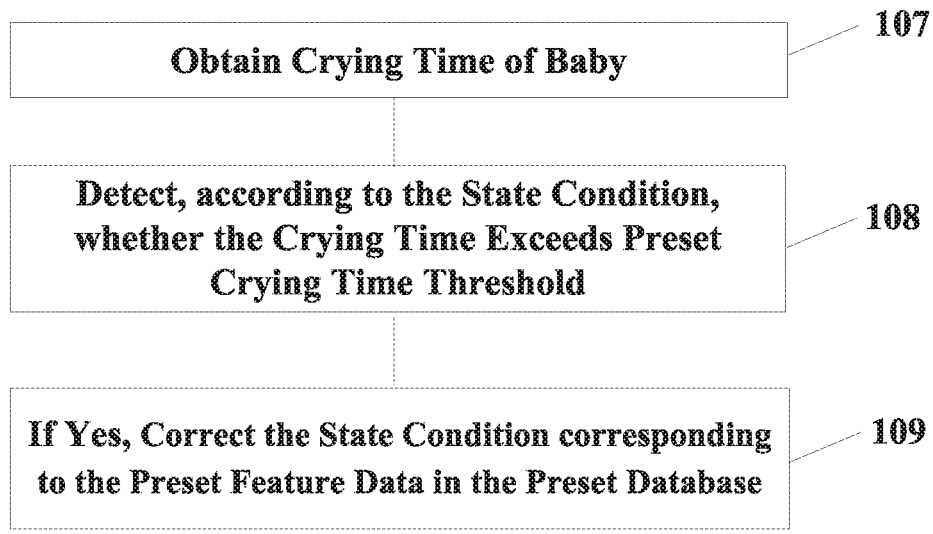
FIG. 8 is a flow chart of a monitoring method according to another embodiment of the present disclosure.

Each baby experiences different behaviors when encountering different state conditions. In order to accurately obtain the state condition of the baby, it is necessary to correct the state corresponding to the preset feature data in real time. In some embodiments, as shown in FIG. 8, the method further includes:

Step 107: obtaining a crying time of the baby;

Step 108, detecting, according to the state condition, whether the crying time exceeds a preset crying time threshold; and Step 109: correcting the state condition corresponding to the preset feature data in the preset database, or outputting correction reminder information.

In general, when parents cope with baby's crying in the right way, the time taken thereon may be relatively short. Therefore, the duration of coping with the baby's crying can be used to judge whether the state condition information of the baby provided by the system is correct, so as to timely correct the information in the preset database to ensure the accuracy of the information in the preset database. For example, when it is known that the baby is moved to the mother by the feature data (for example, the displacement data), the state condition corresponding to the preset feature data in the preset database is a hunger state condition, and the hunger state condition can be fed back to the baby's parents while the crying time of baby is calculated. The baby's parents will cope with the baby's crying in response to the hunger state condition. When the baby stops crying, the baby's parents can judge whether their treatment is correct according to the crying time of the baby. If the baby's crying time exceeds the preset crying time threshold, such as 20 minutes, it can be indicated that the treatment of the baby's parents is not correct. In this case, the state condition (hunger state condition) corresponding to the preset feature data in the preset database may be incorrect. At this point, there is a need to modify this state condition. For example, the state condition may be modified to a bedwetting state. When the state condition corresponding to the feature data occurs to baby again, the state condition fed back to the parents by the monitoring system is a state condition of bedwetting rather than the state condition of hunger. In this way, the parents can cope with the baby's crying with reference to the new state condition, so as to improve the treatment speed of the baby's parents. The monitoring system according to this embodiment can improve the accuracy of the data information in the database by continuously improving the data information in the database. In addition, different state conditions may correspond to different preset crying time thresholds. For example, the preset crying time threshold reflecting a cold or hot state condition may be 2 minutes; and the preset crying time threshold reflecting a state condition of bedwetting or hunger may be 5 minutes.

When the crying time exceeds the preset crying time threshold, in addition to automatically correcting the state of the preset feature data range by the monitoring system, the correction reminder information may also be output to remind the parents or other user to perform a manual correction. The outputting manner of correction reminder information may include, for example, a text or image reminder by using a display device or a voice reminder, which is not specifically limited herein.

After receiving the correction reminder information, the parents or other user of the baby may manually correct the state condition corresponding to the preset feature data in the preset database. At this time, the monitoring method may further include:

Step 112: obtaining the correction information; and

Step 113: correcting the state condition corresponding to the preset feature data in the preset database according to the correction information.

Figure 9:
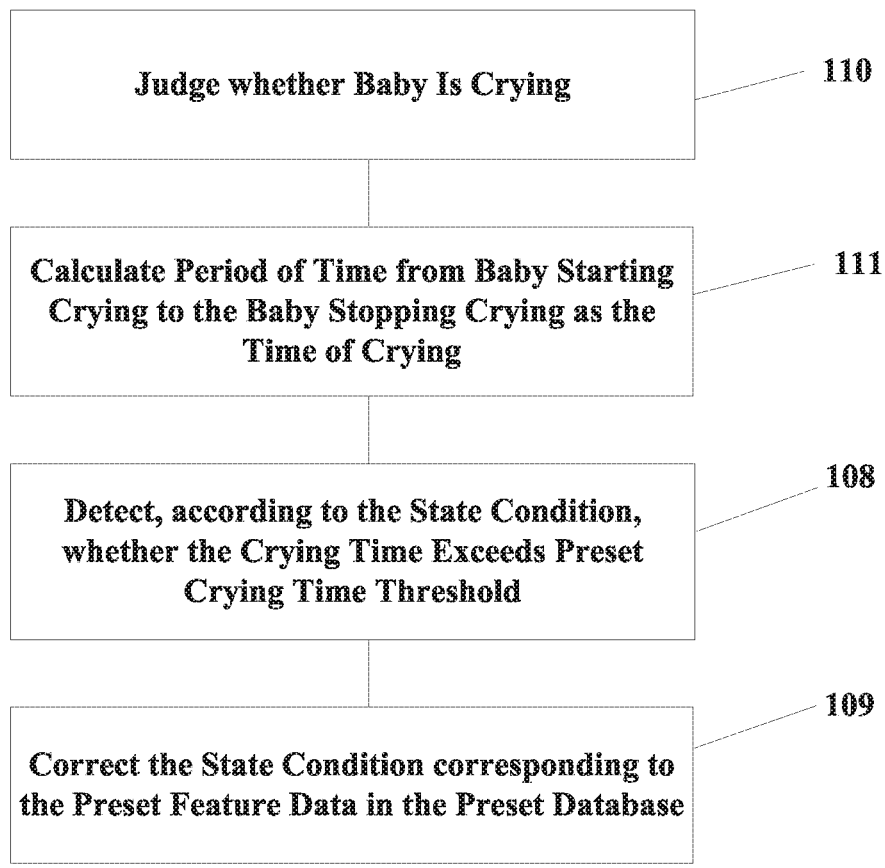
FIG. 9 is a flow chart of a monitoring method according to another embodiment of the present disclosure.

In this embodiment, the state condition corresponding to the preset feature data in the preset database may be corrected by the correction information. For example, the state condition corresponding to the preset feature data may be changed from "hunger" to "bedwetting", and the state condition corresponding to the preset feature data in the preset database may become more accurate by the correction of state condition. There are many ways to obtain the baby's crying time. In some embodiments, as shown in FIG. 9, the step of obtaining the crying time of the baby may include:

Step 110: judging, according to the feature data, whether the baby is crying;

Step 111: calculating a period of time from baby starting crying to the baby stopping crying as the time of crying.

In this embodiment, it is possible to judge whether the baby is crying based on the feature data. For example, when the baby's sound data (far example, decibel) exceeds a set value, it can be determined that the baby is crying, and when the baby's sound data is lower than the set value, it can be determined that the baby stops crying. In addition, a plurality of determination manners may be used, which are not specifically limited herein. Here, the time of crying can be a period of time from the baby starting crying to the baby stopping crying. The feature data is used to accurately calculate the baby's crying time.

The above description is only the specific embodiments of the present disclosure, but the scope of the present disclosure is not limited thereto. Any person skilled in the art can readily conceive changes or alternatives within the technical scope of the disclosure, which are intended to be encompassed therein. Therefore, the scope of the disclosure should be determined by the annexed claims.

The invention claimed is:

1. A monitoring system, comprising:
a collection device, configured to collect feature data of a baby, wherein the collection device includes a displacement collection element configured to collect displacement data of the baby as the feature data, and a pressure collection element configured to collect pressure data of the baby as the feature data; and
a processor, coupled to the collection device and configured to receive the feature data collected by the collection device, determine a state condition of the baby according to the feature data, and output prompt information corresponding to the state condition, wherein the processor is configured to determine the state condition of the baby according to the displacement data including a direction and a distance of displacement and the pressure data on pressure exerted by legs of the baby, wherein the monitoring system further comprises a timing device, coupled to the processor and configured to obtain a crying time of the baby according to the feature data of the baby, and the processor is further configured to receive the crying time and correct the state condition corresponding to preset feature data in a preset database, or output correction reminder information, in response to the crying time exceeding a preset crying time threshold.

2. The monitoring system according to claim 1, further comprising: a storage device, coupled to the processor and configured to store the preset database, the preset database storing preset feature data corresponding to the state condition of the baby, and the processor is configured to determine a state condition corresponding to the preset feature data as the state condition of the baby in the case where the feature data falls within a range of the preset feature data.

3. The monitoring system according to claim 1, further comprising: an input device coupled to the processor and configured to input correction information from a user to correct the state condition corresponding to the preset feature data in the preset database.

4. The monitoring system according to claim 1, wherein the collection device further includes a sound collection element, wherein the sound collection element is configured to collect sound data of the baby as the feature data.

5. The monitoring system according to claim 1, further comprising:

an indication device coupled to the processor and configured to receive the prompt information output by the processor and output an indication corresponding to the prompt information.

6. The monitoring system according to claim 4, wherein the indication device includes at least one of a display element, an audio element and a light element, wherein the display element is coupled to the processor and configured to receive the prompt information output from the processor and provide a display reminder according to the prompt information;

the audio element is coupled to the processor and configured to receive the prompt information output from the processor and provide a sound reminder according to the prompt information; and the light element is coupled to the processor and configured to receive the prompt information output from the processor and provide a light reminder according to the prompt information.

7. A monitoring method, comprising steps of:

obtaining feature data of a baby;

determining a state condition of the baby according to the feature data, wherein the feature data of the baby includes displacement data including a direction and a distance of displacement and pressure data on pressure exerted by legs of the baby; and outputting prompt information corresponding to the state condition, wherein the method further comprises steps of:

obtaining a crying time of the baby;

detecting, according to the state condition, whether the crying time exceeds a preset crying time threshold; and correcting the state condition corresponding to preset feature data in a preset database, or outputting correction reminder information, in response to the crying time exceeding the preset crying time threshold.

8. The method according to claim 7, further comprising:

creating the preset database in which preset feature data corresponding to the state condition of the baby is stored, and the step of determining a state condition of the baby according to the feature data includes:

detecting the presence of preset feature data corresponding to the feature data; and determining a state condition corresponding to the preset feature data as the state condition of the baby in the case where the feature data falls within a range of the preset feature data.

9. The method according to claim 7, further comprising:

obtaining correction information; and correcting the state condition corresponding to the preset feature data in the preset database according to the correction information.

10. The method according to claim 7, wherein the feature data of the baby further includes sound data of the baby.

11. The method according to claim 7, wherein the prompt information includes at least one of image prompt information, sound prompt information, and light prompt information.

* * * * *